United States Patent [19]
Zeitlin et al.

[11] Patent Number: 5,908,850
[45] Date of Patent: Jun. 1, 1999

[54] METHOD OF TREATING ATTENTION DEFICIT DISORDERS WITH D-THREO METHYLPHENIDATE

[75] Inventors: Andrew L. Zeitlin, Millington; Maghsoud M. Dariani, Fanwood; David I. Stirling, Branchburg, all of N.J.

[73] Assignee: Celgene Corporation, Warren, N.J.

[21] Appl. No.: 08/827,230

[22] Filed: Apr. 2, 1997

Related U.S. Application Data

[63] Continuation of application No. 08/567,131, Dec. 4, 1995, abandoned.

[51] Int. Cl.$^6$ .................................................. A61K 31/445
[52] U.S. Cl. ............................................................. 514/315
[58] Field of Search ............................................. 514/315

[56] References Cited

U.S. PATENT DOCUMENTS

| | | | |
|---|---|---|---|
| 2,507,631 | 5/1950 | Hartmann et al. | 260/294 |
| 2,957,880 | 10/1960 | Rometsch | 546/233 |
| 4,992,445 | 2/1991 | Lawter et al. | 514/279 |
| 5,104,899 | 4/1992 | Young et al. | 514/646 |
| 5,114,946 | 5/1992 | Lawter et al. | 514/279 |
| 5,217,718 | 6/1993 | Colley et al. | 424/449 |
| 5,283,193 | 2/1994 | Yamamoto et al. | 435/280 |
| 5,284,769 | 2/1994 | Evans et al. | . |
| 5,331,000 | 7/1994 | Young et al. | 514/570 |
| 5,362,755 | 11/1994 | Barberich et al. | 514/649 |
| 5,375,693 | 12/1994 | Woosley et al. | 514/317 |
| 5,449,743 | 9/1995 | Kobayashi et al. | 528/355 |

FOREIGN PATENT DOCUMENTS

| | | |
|---|---|---|
| WO 97/03671 | 2/1997 | WIPO . |
| WO 97/03672 | 2/1997 | WIPO . |
| WO 97/03673 | 2/1997 | WIPO . |

OTHER PUBLICATIONS

Angrist et al. *Journal of Clinical Phsychopharmacology*, 1992 12:268–272.
Barkley et al. *Pediatrics* 1990 86:184–192.
Barkley et al. *Pediatrics* 1991 87:519–531.
Golinko *Neuro–Psychopharmacol. & Biol Phsychiat* 1984 8:1–8.
Greenhill *Pediatric Psychopharmacology* 1992 15:1–27.
Scott *Drug Safety* 1993 8:149–159.
White et al. *J. Clin. Phsychiatry* 1992 53:153–156.
Biosis Abstract No.: 87129969 Holmes et al. Psychostimulant Response in Aids–Related Complex Patients *J. Clin. Psychiatry* 50(1):5–8 (1989).
Biosis Abstract No.: 95066168 Srinivas et al. Enantioselective Pharmacolinetics and Pharmacodynamics of Racemic Threo–Methylphenidate in Children with Attention Deficit Hyperactivity Disorder *Clin. Pharmacol. Ther* 52(2):561–568 (1990).

Bowden et al. Reactions of Carbonyl COmpounds in Basic SOlutions The Alkaline Hydrolysis of N–Methyl, N–Phenyl, and Bicyclo Lactams Penicillins, and N–Alkyl–N–methylacetamides *J. Chem. Soc. Perkin Trans.* 1990 12:2111–2116.
Ding et al., Cis– and trans–Axetidin–2–ones from Nitrones and Copper Acetylide *J. Chem. Soc. Perkin* 1976 22:2382–2386.
Brown, C. Chirality in Drug Design and Synthesis Academic Press Inc. 1990 4–7.
Klibanov A.M. Asymmetric Transformations Catalyzed by Enzymes in Organic Solvents *Acc. Chem. Res.* 1990 23:114–120.
Earle et al. J. Chem. Soc. 1969:2093 (1980).
Srinivas et al. Enantiomeric Gas Chromatography Assay with Electron Capture Detection for d–Ritalinic Acid in Plasma, J. Chromatagraph 1990 530:327–336.
Srinivas et al. Sterioselective Disposition of Methylphenidate in Children with Attention Deficit Disorder J. Pharmacol. Exp. Ther. 1987 241:300–306.
Corey et al. J. Amer. Chem. Soc 1965 87:2518.
Moll F. Naturforsch Teil B. 1966 21:297.
Greenhill Pediatric Psychopharmacology 1992 15:1–27.
Scott Drug Safety 1993 8:149–159.
White et al. J. Clin. Psychiatry 1992 53:153–156.
Greenhill L. Attention–Deficit Hyperactivity Disorder Child & Adol. Psych. Clin. N.A., 1995 4:123–165.
Navia et al. Annals of Neurology 1986 19:517–524.
Douzenis et al. Proc 7th. Int'l. Conf. AIDS 1991 1:2135–2215.
Aoyama et al. Pharmacolinetics and pharmacodynamics of (+)–threo–methylphenidate enantiomer in patients with hypersomnia Clin. Pharmacol. Ther 1994 55:270–276.
Uetrecht et al. Pharmacol Res. 1989 6:265–273.
Staal et al. Lancet 1992 339:909–912.
Rieder et al. Ann. Intern Med. 1989 110:286–289.
Patrick et al. J. Pharmacol & Exp. Terhap. 1987 241:152–158.
Srinivas et al. Pharmacol Res. 1993 10:14–21.
Brown G. Int'l J. Psychiatry Med. 1995 25:21–37.

*Primary Examiner*—Raymond Henley, III
*Attorney, Agent, or Firm*—Woodcock Washburn Kurtz Mackiewicz & Norris LLP

[57] ABSTRACT

Methods for treating Attention Deficit Disorder, Attention Deficit Hyperactivity Disorder, AIDS Dementia Complex and cognitive decline in HIV-AIDS while minimizing drug hypersensitivity, toxicity, side effects, euphoric effect, and drug abuse potential by administration of d-threo-methylphenidate or pharmaceutically acceptable salts thereof.

4 Claims, No Drawings

METHOD OF TREATING ATTENTION DEFICIT DISORDERS WITH D-THREO METHYLPHENIDATE

This is a continuation of application Ser. No. 08/567,131, filed Dec. 4, 1995, now abandoned, disclosure of which is herein incorporated by reference.

The present invention relates to methods of treating certain Central Nervous System disorders such as Attention Deficit Disorder (ADD), Attention Deficit Hyperactivity Disorder (ADHD), HIV/AIDS cognitive decline, and AIDS Dementia Complex with decreased side effects, reduced euphoric effect, and reduced drug abuse potential.

BACKGROUND OF THE INVENTION

Attention Deficit Disorder (ADD) is the most commonly diagnosed illness in children. Patrick et al., *J. Pharmacol. & Exp. Therap.*, 241:152–158 (1987). Symptoms of ADD include distractibility and impulsivity. A related disorder, termed Attention Deficit Hyperactivity Disorder (ADHD), is further characterized by increased symptoms of hyperactivity in patients. Racemic methylphenidate (e.g., Ritalin®) is a mild Central Nervous System stimulant with pharmacological activity qualitatively similar to amphetamines, and has been the drug of choice for symptomatic treatment of ADD in children. Greenhill, L., *Child & Adol. Psych. Clin. N.A.*, Vol. 4, Number 1:123–165 (1995). Current administration of racemic methylphenidate, however, results in notable side effects such as anorexia, weight loss, insomnia, dizziness and dysphoria. Additionally, racemic methylphenidate which is a Schedule II controlled substance, produces a euphoric effect when administered intravenously or through inhalation, and thus carries a high potential for substance abuse in patients.

At least 70% of HIV-infected individuals who have developed Acquired Immunodeficiency Syndrome (AIDS) eventually manifest cognitive defects, and many display signs and symptoms of dementia. See Navia et al., *Annals of Neurology*, 19:517–524 (1986). Complaints of forgetfulness, loss of concentration, fatigue, depression, loss of attentiveness, mood swings, personality change, and thought disturbance are common in patients with Human Immunodeficiency Virus (HIV) disease. Douzenis et al., *Proc. 7th Int'l. Conf. AIDS*, 1, MB, 2135:215 (1991); Holmes et al., *J. Clin. Psychiatry*, 50:5–8 (1989). Racemic methylphenidate has been used to treat cognitive decline in AIDS/ARC patients. Brown, G., *Intl. J. Psych. Med.* 25(1): 21–37 (1995). As described above, racemic methylphenidate which is a Schedule II controlled substance, produces a euphoric effect when administered intravenously or through inhalation, and thus carries a high potential for drug abuse in AIDS patients.

Glutathione is an important antioxidative agent that protects the body against electrophilic reactive compounds and intracellular oxidants. It has been postulated that HIV-AIDS patients suffer from drug hypersensitivity due to drug overload and an acquired glutathione deficiency. See Uetrecht et al., *Pharmacol. Res.*, 6:265–273 (1989). Patients with HIV infection have demonstrated a reduced concentration of glutathione in plasma, cells and broncho-alveolar lavage fluid. Staal et al., *Lancet*, 339:909–912 (1992). Clinical data suggests that HIV-seropositive individuals display adverse reactions to the simultaneous administration of several otherwise therapeutic drugs. Rieder et al., *Ann. Intern. Med.*, 110:286–289 (1989). It is therefore desirable to provide for the administration of methylphenidate in reduced dosages among patients with drug hypersensitivity due to HIV infection.

Methylphenidate possesses two centers of chirality and thus can exist as four separate optical isomers. The four isomers of methylphenidate are as follows:

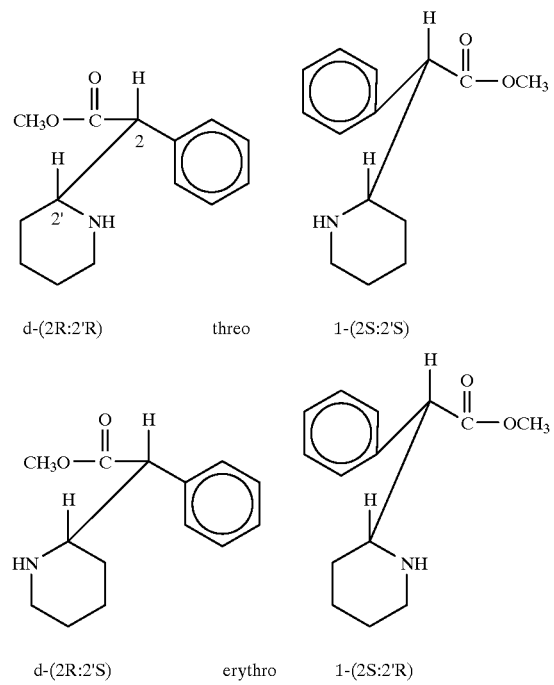

Diastereomers are known in the art to possess differing physical properties, such as melting point and boiling point. For example, while the threo- racemate of methylphenidate produces the desired Central Nervous System action, the erythro- racemate contributes to hypertensive side effects and exhibits lethality in rats.

Additional studies in animals, children and adults have demonstrated pharmacological activity in the d-threo isomer of methylphenidate (2R:2'R) . See Patrick et al., *J. Pharmacol. & Exp. Therap.*, 241:152–158 (1987). Although the role of the l-isomer in toxicity or adverse side effects has not been thoroughly examined, the potential for isomer ballast in methylphenidate is of concern for many patient groups, particularly those drug hypersensitive patients as described above.

Although l-threo-methylphenidate is rapidly and stereoselectively metabolized upon oral administration, intravenous administration or inhalation results in high l-threo-methylphenidate serum levels. Srinivas et al., *Pharmacol. Res.*, 10:14–21 (1993). Intravenous administration and inhalation are the methods of choice by drug abusers of current methylphenidate formulations. The present invention postulates that the euphoric effect produced by current formulations of methylphenidate is due to the action of l-threo-methylphenidate.

Accordingly, it has been discovered that the use of the d-threo isomer (2R:2'R) of methylphenidate, substantially free of the l-threo isomer produces a methylphenidate medication which retains high activity levels and simultaneously possesses reduced euphoric effect and reduced potential for abuse among patients.

U.S. Pat. No. 2,507,631, to Hartmann et al. describes methylphenidate and processes for making the same.

U.S. Pat. No. 2,957,880, to Rometsch et al. describes the conversion of α-aryl-α-piperidyl-(2)-acetic acids and derivatives thereof (including methylphenidate) into their respective racemates.

Holmes et al., *J. Clin. Psychiatry,* 50:5–8 (1989) reported on the use of racemic methylphenidate (Ritaline®) and dextroamphetamines in the treatment of cognitive impairment in AIDS patients.

Srinivas et al., *J. Pharmacol. & Exp. Therap.,* 241:300–306 (1987) described use of racemic dl-threo-methylphenidate (Ritalin®) in the treatment of ADD in children. This study noted a 5-fold increase in plasma levels of d-threo-methylphenidate in children treated with racemic methylphenidate, but was otherwise inconclusive with regard to the efficacy of a single methylphenidate isomer at therapeutically significant doses.

Srinivas et al., *Clin. Pharmacol. Ther.,* 52:561–568 (1992) studied the administration of dl-threo, d-threo and l-threo-methylphenidate to children suffering from ADHD. While Srinivas et al. reported the pharmacodynamic activity of dl-threo-methylphenidate resides in the d-threo isomer, this study investigated neither the adverse side effects of the l-threo isomer, nor the euphoric effects of the single isomers or racemate. Single isomer dosages below ½ of the racemate dosage were not studied.

Patrick et al., *J. Pharmacol. & Exp. Therap.,* 241:152–158 (1986) examined the pharmacology of the enantiomers of threo-methylphenidate, and assessed the relative contribution of each isomer to central and peripheral actions of Ritalin®.

Brown, G., *Intl. J. Psych. Med.,* 25(1):21–37 (1995) reported the use of racemic methylphenidate for the treatment of AIDS cognitive decline.

Patrick et al., *Psychopharmacology: The Third Generation of Progress,* Raven Press, N.Y. (1987) examined the pharmacokinetics and actions of methylphenidate in the treatment of Attention Deficit Hyperactivity Disorder (ADHD). Patrick noted the d-threo isomer possesses higher activity than the l-threo isomer, and that d-threo methylphenidate may be responsible for the therapeutic activity in the racemic drug.

Aoyama et al., *Clin. Pharmacol. Ther.,* 55:270–276 (1994) reported on the use of (+)-threo-methylphenidate in the treatment of hypersomnia. Aoyama et al. describe a correlation between sleep latency in patients and plasma concentration or (+)-threo-methylphenidate.

SUMMARY OF THE INVENTION

The present invention is based on the discovery that d-threo-methylphenidate (2R:2'R) possesses enhanced therapeutic activity with reduced side effects, and l-threo-methylphenidate produces undesirable side effects, euphoria and drug abuse potential in patients suffering from Attention Deficit Disorder, Attention Deficit Hyperactivity Disorder, AIDS cognitive decline, and AIDS Dementia Complex.

The present invention thus relates to methods of treating Attention Deficit Disorder and Attention Deficit Hyperactivity Disorder in children and adults while providing for reduced side effects, reduced euphoric effect and reduced potential for abuse potential through administration of d-threo-methylphenidate (2R:2'R) of the formula:

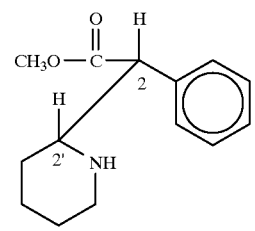

or a pharmaceutically acceptable salt thereof, substantially free of the l-threo isomer.

The invention further relates to methods of treating AIDS-related dementia and related cognitive disorders while providing for reduced side effects, reduced euphoric effect, and reduced abuse potential through administration of d-threo-methylphenidate (2R:2'R) of the formula:

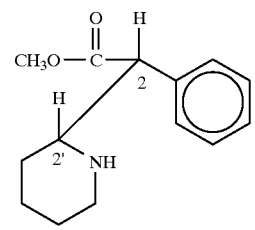

or a pharmaceutically acceptable salt thereof, substantially free of the l-threo isomer.

Prescription of methylphenidate to treat AIDS cognitive decline and AIDS Dementia Complex associated with HIV infection is becoming increasingly popular. However, high doses in excess of 40 mg/day are not well tolerated by a substantial number of HIV-infected patients when treated over weeks or months. Brown, G., *Int'l J. Psychiatry. Med.,* 25:21–37 (1995). The d-threo isomer use of the present invention thus enables a lowered dosing therapy resulting in improved efficacy for diseased patients and particularly HIV-infected patients.

Moreover, administration of the d-threo isomer to patients will result in decreased side effects, reduced euphoric effect, and substantially reduce the potential for abuse of the product.

DETAILED DESCRIPTION OF THE INVENTION

Racemic methylphenidate and its individual isomers are known. See U.S. Pat. Nos. 2,507,631 and 2,957,880. They can be prepared by conventional techniques, and can be obtained from a variety of commercial sources.

The d-threo isomer of the present invention can be administered orally, rectally, parenterally, or transdermally, alone or in combination with other psychostimulants, antidepressants, and the like to a patient in need of treatment. Oral dosage forms include tablets, capsules, dragees, and similar shaped compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter. Transdermal administration can be effected through the use of transdermal patch delivery systems and the like. The preferred routes of administration are oral and parenteral.

The dosage employed must be carefully titrated to the patient, considering age, weight, severity of the condition, and clinical-profile. Typically, the amount of d-threo-methylphenidate administered will be in the range of 5–50 mg/day, but the actual decision as to dosage must be made by the attending physician.

The present invention provides enhanced relief for patients suffering from Attention Deficit Disorder and Attention Deficit Hyperactivity Disorder while providing for reduced side effects, reduced euphoric effect, and reduced abuse potential through administration of d-threo-methylphenidate substantially free of the l-threo isomer.

The invention further provides for treatment of AIDS-related dementia and related cognitive disorders with d-threo-methylphenidate substantially free of the l-threo isomer while providing for reduced side effects, reduced euphoric effect, and reduced abuse potential.

The term, "substantially free of the l-threo-isomer" means that the composition contains at least 90% by weight of d-threo-methylphenidate, and 10% by weight of l-threo-methylphenidate. In the most preferred embodiment, the term "substantially free of the l-threo isomer" means that the composition contains at least 99% by weight of d-threo-methylphenidate and 1% or less of l-threo-methylphenidate.

The following examples will serve to further typify the nature of the invention, but should not be construed as a limitation on the scope thereof, which is defined solely by the appended claims.

EXAMPLE 1

Tablets for chewing, each containing 5 milligrams of d-threo-methylphenidate, can be prepared in the following manner:

| Composition (for 1000 tablets) | |
|---|---|
| d-threo-methylphenidate | 5.00 grams |
| mannitol | 15.33 grams |
| lactose | 10.00 grams |
| talc | 1.40 grams |
| glycine | 0.83 grams |
| stearic acid | 0.66 grams |
| saccharin | 0.10 grams |
| 5% gelatin solution q.s. | |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The d-threo-methylphenidate, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 2

Tablets, each containing 10 milligrams of d-threo-methylphenidate, can be prepared in the following manner:

| Composition (for 1000 tablets) | |
|---|---|
| d-threo-methylphenidate | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water q.s. | |

The solid ingredients are first forced through a sieve of 0.6 mm mesh width. Then the d-threo-methylphenidate, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 3

Gelatin dry-filled capsules, each containing 20 milligrams of d-threo-methylphenidate, can be prepared in the following manner:

| Composition (for 1000 capsules) | |
|---|---|
| d-threo-methylphenidate | 20.0 grams |
| microcrystalline cellulose | 6.0 grams |
| sodium lauryl sulfate | 0.4 grams |
| magnesium stearate | 1.6 grams |

The sodium lauryl sulfate is sieved into the d-threo-methylphenidate through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 28 milligrams each into size 0 (elongated) gelatin dry-fill capsules.

EXAMPLE 4

A 0.2% injection or infusion solution can be prepared, for example, in the following manner:

| | |
|---|---|
| d-threo-methylphenidate | 5.0 grams |
| sodium chloride | 22.5 grams |
| phosphate buffer pH 7.4 | 300.0 grams |
| demineralized water to 2500 mL. | |

The d-threo-methylphenidate is dissolved in 1000 milliliters of water and filtered through a microfilter or slurried in 1000 mL of $H_2O$. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of d-threo-methylphenidate).

What is claimed is:

1. A method of treating at least one of Attention Deficit Disorder and Attention Deficit Hyperactivity Disorder and providing enhanced therapeutic activity, reduced side effects euphoric effect, or potential for drug abuse as compared to racemic threo methylphenidate, said method comprising administering to a human exhibiting symptoms of such disorder therapeutically effective amounts of D-threo methylphenidate or pharmaceutically acceptable salt thereof, substantially free of L-threo methylphenidate, on a daily basis.

2. The method according to claim 1 wherein the amount administered is 5 mg to 50 mg per day.

3. The method according to claim 1 wherein the amount of d-threo-methylphenidate or a pharmaceutically acceptable salt thereof is greater than 99% by weight.

4. The method according to claim 1 wherein said D-threo methylphenidate is administered together with a pharmaceutically acceptable carrier.

* * * * *